(12) United States Patent
Petrides (10) Patent No.: US 11,701,469 B2
(45) Date of Patent: Jul. 18, 2023

(54) DEVICES AND METHODS FOR CONDUIT DISTENTION

(71) Applicant: Matthew John Petrides, Sea Girt, NJ (US)

(72) Inventor: Matthew John Petrides, Sea Girt, NJ (US)

( * ) Notice: Subject to any disclaimer, the term of this patent is extended or adjusted under 35 U.S.C. 154(b) by 478 days.

(21) Appl. No.: 16/860,020

(22) Filed: Apr. 27, 2020

(65) Prior Publication Data
US 2020/0338270 A1    Oct. 29, 2020

Related U.S. Application Data

(60) Provisional application No. 62/838,602, filed on Apr. 25, 2019.

(51) Int. Cl.
*A61M 5/20*    (2006.01)
*A61M 5/32*    (2006.01)
(Continued)

(52) U.S. Cl.
CPC .......... *A61M 5/2053* (2013.01); *A61M 5/204* (2013.01); *A61M 5/2033* (2013.01); *A61M 5/3158* (2013.01); *A61M 5/3202* (2013.01); *A61M 2005/1787* (2013.01); *A61M 2005/2026* (2013.01); *A61M 2005/3114* (2013.01);
(Continued)

(58) Field of Classification Search
CPC .. A61M 5/2053; A61M 5/2033; A61M 5/204; A61M 5/3158; A61M 5/3202; A61M 2005/1787; A61M 2005/2026; A61M 2005/3114; A61M 2205/0216; A61M 2205/3341; A61M 2005/202; A61M 2005/3128; A61M 2205/15; A61M 2209/04; A61M 2005/1403;
(Continued)

(56) References Cited

U.S. PATENT DOCUMENTS 5,024,662 A  *  6/1991  Menes ............... A61B 17/3401
                                                    604/218
5,429,607 A  *  7/1995  McPhee ............... A61M 5/1454
                                                    604/131
(Continued)

FOREIGN PATENT DOCUMENTS

| | | |
|---|---|---|
| CN | 201253357 Y | 6/2009 |
| EP | 1495776 A1 | 12/2008 |
| EP | 3386562 B1 | 7/2019 |

OTHER PUBLICATIONS

Catalog JT Construction Chemicals, Jun. 2017, pp. 1-2, Korea.

*Primary Examiner* — Amber R Stiles
*Assistant Examiner* — Nelson Louis Alvarado, Jr.
(74) *Attorney, Agent, or Firm* — Craig Litherland (57) ABSTRACT

Devices and methods are disclosed that provide a syringe actuator device for use in the distention and irrigation of a body conduit before the use in a medical procedure such as a coronary bypass graft procedure. The device can be retrofit to a syringe by attaching it to the cap of the plunger and engaged to automatically apply pressure to fluid in the syringe. In some embodiments, elastic bands attached to the device are easily engaged or removed from a syringe during a procedure to limit the pressure on the syringe to various levels. The device may be overridden by an operator pushing on the plunger of the syringe as in normal syringe operation.

18 Claims, 11 Drawing Sheets

(51) Int. Cl.
*A61M 5/315* (2006.01)
*A61M 5/178* (2006.01)
*A61M 5/31* (2006.01)

(52) U.S. Cl.
CPC ............... *A61M 2205/0216* (2013.01); *A61M 2205/3341* (2013.01)

(58) Field of Classification Search
CPC ........ A61M 39/225; A61M 1/70; A61M 1/84; A61M 1/86; A61M 1/88; A61M 1/912; A61M 27/00
See application file for complete search history.

(56) References Cited

U.S. PATENT DOCUMENTS

| | | |
|---|---|---|
| 5,531,696 A | 7/1996 | Menes |
| 5,643,213 A | 7/1997 | McPhee |
| 5,681,283 A | 10/1997 | Brownfield |
| 5,944,693 A | 8/1999 | Jacobs |
| 2006/0106342 A1 | 5/2006 | Cox |
| 2008/0319393 A1* | 12/2008 | Elder .................. A61M 5/1454 604/151 |

* cited by examiner

SECTION A

DEVICES AND METHODS FOR CONDUIT DISTENTION

RELATED APPLICATIONS

The present application claims priority to U.S. Provisional Patent Application No. 62/838,602, the entirety of which is incorporated herein by reference.

TECHNICAL FIELD

The present disclosure generally relates to methods and devices for pressurizing bodily tissue and, more particularly to methods and devices for pressurizing a venous or arterial conduit.

BACKGROUND

The Injection of fluid under pressure is commonly performed in medicine and surgery. Pressurized fluid is injected into bodily tissue, anatomic organs, blood vessels, ducts, and other tubular structures within the patient, as well as various medical devices. For example, pressurized fluid may be injected into a venous or arterial conduit harvested from a patient for use as a bypass graft to identify potential areas of leakage due to un-ligated branches, perforation sites, or attenuated wall. Pressurized fluid may be injected into the ureter for its identification and localization during open abdominal surgery or laparoscopic surgery.

Pressurized fluid may be injected into the external auditory canal during routine diagnostic examination or examination of an inner ear infection. Pressurized fluid may be injected into a balloon catheter used for arterial embolectomy or venous thrombectomy. In all of these situations, over-pressurization with fluid may cause trauma or injury to body tissue or structures. In the case of a coronary bypass conduit harvested from the patient, over-pressurization may have severe consequences such as graft failure, with resultant myocardial infarction and even death. Fluid injection devices with pressure limitation have been previously described. Some of these devices contain pressure relief valves that vent pressurized fluid outside the of the injection device at a predetermined pressure. Other devices may contain an elastic reservoir, such as a balloon, in fluid communication with the syringe. The elastic reservoir expands or balloons out when the pressure in the syringe exceeds a specific value to limit the applied pressure. In such designs, it is difficult or impossible to provide injection pressure exceeding the level set by the elasticity of the balloon.

Conventional pressure-limiting syringes can involve complicated devices and mechanisms that may be expensive; these injection devices provide an injection pressure that is set to a pre-determined level, above that level the injection fluid is either displaced or vented to maintain the preset value. However, in clinical practice, it is often desirable to exert an injection pressure into a body structure or a medical device that slightly exceeds the preset pressure of the pressure-limiting injection device. Slight over-pressurization may be required for anatomic situations that may vary from patient to patient. For example, during the preparation of a vein graft for coronary bypass, one patient may have veins that exhibit less compliance than normally encountered due to increased vein wall thickness. The clinician may wish to modulate the injection pressure by providing a pressure slightly higher than the preset level of the device. The ability to modulate the injection pressure while providing tactile feedback of the degree of increased pressure is of clinical importance, to achieve adequate vein distention without vessel over-inflation and barotrauma. Thus, there is a need for a simple, low-cost device that provides the application of pressure to a conduit while having the option for manual override.

SUMMARY

Broadly, the invention provides a novel syringe actuator device with few parts that can be retrofitted onto a standard syringe or manufactured as part of a syringe. According to some embodiments, the device comprises a cap having a proximal end and a distal end, a recess in the distal end of the cap, the recess capable of securing onto a plunger flange of a syringe. The device may be retained on the syringe solely by the connection between the plunger flange and the recess. The device comprises at least one elastic band connected to the cap such that the elastic band is capable of connecting to a barrel flange of the syringe to apply a force between the cap and the barrel flange.

Optionally, the device is capable of fitting onto the plunger flange by an interference fit or being restrained by a rim disposed inside of the recess for capturing the plunger flange. The elastic band comprises a first elastic band connected to a first side of the cap and a second elastic band connected to an opposite side of the cap, and each elastic band may be individually attached to the barrel flange to apply different forces to the plunger flange. Optionally, the device may be made as a unitary part that may be made by injection molding, and it may be made of a thermoplastic elastomer.

According to some embodiments of the present invention, there is provided a method for preparing a conduit. The order of operations in the following methods may vary from the order described, as the steps may be performed in a different order while remaining within the scope of the invention. The method comprises providing a syringe actuator having a cap and elastic bands for providing hands-free pressurization of a syringe. Attaching the cap to a plunger flange of a syringe and filling the syringe with fluid, connecting the syringe to a stopcock and a vein cannula, and attaching at least one elastic band to the barrel flange of the syringe to apply pressure to the fluid in the syringe. A stopcock may be opened to flush the conduit, followed by tying or clipping branches of the conduits that are leaking, placing a soft clamp on the distal end of the conduit, and removing the elastic band from the barrel flange while keeping the cap attached to the plunger flange. Next, the syringe may be refilled and the stopcock closed followed by attaching at least one elastic band to the barrel flange, and then tying or clipping branches that are leaking.

Optionally, pressure applied by the elastic band may be overridden by pressing on the cap. Next the elastic band may be removed from the barrel flange so that the syringe may be filled again. Next, one elastic band is attached to the barrel flange so that the conduit may be allowed to completely distend under low pressure.

Optionally, the cap may be fitted onto the plunger flange by an interference fit, or alternatively, the cap may have a rim disposed inside of the recess for capturing the plunger flange. The elastic band comprises a first elastic band connected to a first side of the cap and a second elastic band connected to an opposite side of the cap. Each elastic band may be individually attached to the barrel flange to apply different forces to the plunger flange.

Another method for preparing a conduit is provided, which includes using a syringe having built-in elastic bands. First, providing a syringe having a plunger flange and a barrel flange, wherein the plunger flange has at least one elastic band permanently attached. The syringe may be filled with fluid and connected to a stopcock and a vein cannula before attaching the at least one elastic band to the barrel flange of the syringe to apply pressure to the fluid in the syringe. The stopcock may be opened to flush the conduit, followed by tying or clipping branches of the conduit that are leaking. A soft clamp may be placed on the distal end of the conduit before removing an elastic band from the barrel flange and refilling the syringe and closing the stopcock so fluid does not expel from the syringe. One or more elastic bands may be attached to the barrel flange, followed by, again, tying or clipping branches that may be leaking.

Optionally, the pressure applied by the elastic band may be overridden by pressing on the cap. The elastic bands may be removed from the barrel so that the syringe may be refilled. Finally, one elastic band may be attached to the barrel flange to allow the conduit to completely distend under the relatively low pressure applied by one band. The plunger flange may comprise a first elastic band connected to a first side of the plunger flange and a second elastic band connected to an opposite side of the plunger flange; each elastic band may be individually attached to the barrel flange to apply different forces to the plunger flange. Optionally, the plunger flange and the elastic band may be made as one unitary part, which may be made by injection molding, or the elastic band may be overmolded with the plunger flange.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments follows.

Embodiments will now be described with reference to the accompanying drawings, which show some, but not all of the disclosed embodiments. While this invention has been particularly shown and described with references to example embodiments thereof, it will be understood by those skilled in the art that various changes in form and details may be made therein without departing from the scope of the invention encompassed by the appended claims. Furthermore, while several embodiments are described, the scope of the embodiments should not be construed to be limited to those set forth herein.

For the purposes of this disclosure, the terms "proximal" and "distal" are used with reference to the device, that is, "proximal" denotes the region near the plunger of a syringe and "distal" denotes the of the region away from the handle toward and beyond the tip of the syringe.

The embodiments disclosed generally describe a syringe actuator that provides hands-free operation of a syringe with override ability and multiple force levels of force adjustment for precise control of fluid flow and pressure.

Figure 1:
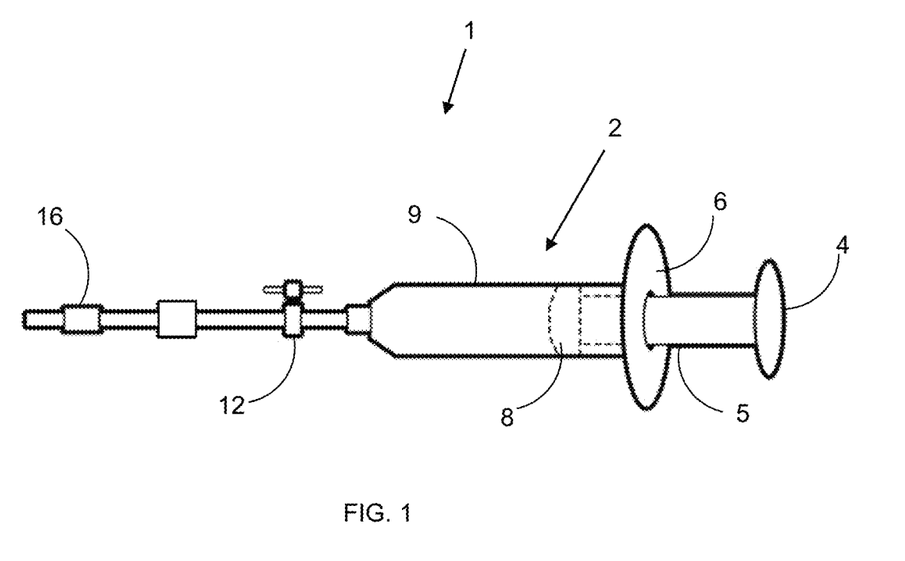
FIG. 1 shows an exemplary conduit distention system.

Referring to FIG. 1, a typical conduit distention and irrigation system is shown for context. The main components of the system 1 are a syringe 2, a stopcock 12 (one-way), and a cannula 16, though additional components and connectors are used in such procedures, and customization is typical. For example, some operators do not use a stopcock 12 in some procedures. The syringe 2 is a typical disposable syringe which may have any fluid volume capacity; for example, a fluid capacity of 20 cc is common in conduit distention procedures such as in saphenous vein graft preparation for cardiovascular bypass procedures. The syringe includes a plunger 5 with an attached plunger flange 4 at the proximal end, a piston 8 attached to the distal end of the plunger 5, and a barrel 9 having a barrel flange 6 at the proximal end of the barrel 9.

Figure 2A:
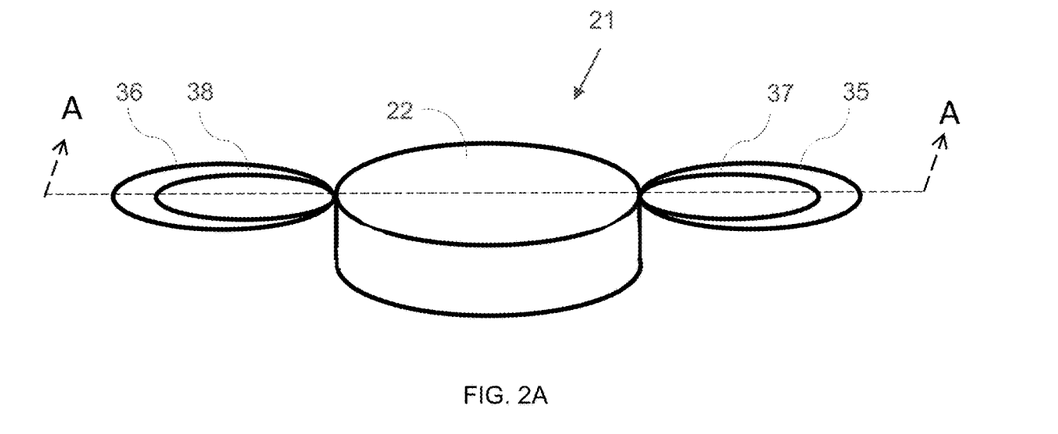
FIG. 2A shows an embodiment of a syringe actuator having four elastic bands.

FIGS. 2A-2D show various embodiments of a syringe actuator that is capable of attaching to a standard syringe plunger flange via a recess in the cap of the syringe actuator. These embodiments may have multiple elastic bands to titrate the force applied to the syringe. For example, the embodiment shown in FIG. 2A is a syringe actuator 21 which has four elastic bands attached to a plunger cap 22: first elastic band 35 and second elastic band 36 are disposed on opposite sides of the plunger cap 22, while the third elastic band 37, and fourth elastic band 38 are disposed on opposite sides of the third elastic band 37. The elastic bands 35, 36, 37, and 38, are capable of attaching to a barrel flange of a syringe by being hooked over the barrel flange. The bands may be sized such that their free, unloaded length is shorter than the maximal distance between the plunger flange and barrel flange when the syringe is full. Thus, when the syringe is filled with some level of fluid, the bands are deformed in tension which causes them to apply a force between the plunger flange and the barrel flange, thus increasing the pressure on the fluid in the syringe. Even when the bands are engaged, the operator may still apply force to the plunger cap manually to override the applied pressure when desired. The operation of syringe actuator embodiments is described in more detail below.

This arrangement, having multiple elastic bands, allows the medical operator to titrate the level of pressure by attaching different combinations of bands; the system is "pressure limiting." Once the bands are in place, the syringe can be left "hands-off," enabling the operator to perform other aspects of a procedure concurrently. For example, for preparation of a vein graft for coronary bypass, an operator may initially desire to apply a pressure of 90 mmHg to examine the graft for leaks, and if the particular graft requires more pressure, he or she may wish to apply higher pressures, therefore, he or she may apply pressure manually. In some cases, the pressure applied by the syringe actuator is recommended to not exceed 270 mmHg for example, because pressures at this level may incur risks such as breaching the wall of the graft. As no two vessels are alike with regard to their wall thickness and potential wall breaches (leaks), their ability to withstand applied fluidic pressure varies. Therefore, the operator may apply the first elastic band 35 which provides a force equating to 90 mmHg of fluid pressure, and then apply the second elastic band 36, which also provides a force equating to another 90 mmHg, resulting in 180 mmHg of applied pressure. If more pressure is desired, the third elastic band 37 may be applied, which may be capable of applying 90 mmHg alone, resulting in a total of 270 mmHg. Finally, the fourth elastic band 38 may be capable of applying 90 mmHg alone and may be added to increase the applied pressure to 360 mmHg.

Thus, many levels of pressure may be applied depending on the operator's needs. The elastic bands may each have the same stiffness curve, and hence the same maximum pressure when applied individually, or they may be capable of applying different pressures when individually applied, thus changing the increments of pressure available to the operator. For example, the first elastic band 35 and the second elastic band 36 may each be capable of applying 45 mmHg of pressure so that when applied together they result in 90 mmHg of applied pressure. Next, the third elastic band 37 and the fourth elastic band 38 may each be capable of 90 mmHg, so that the operator has two additional levels at his or her avail (180 mm Hg and 270 mmHg) beyond the initial 90 mmHg applied by the first two elastic bands. The bands may be applied in any order so that the many combinations are available that can produce many different pressure increments. In general, the operator may apply manual override pressure regardless of the number of bands in use, and hence pressure level, allowing him or her to more precisely test the conduit.

One skilled in the art would recognize that the amount of force applied to the plunger by an elastic element in tension is proportional to various factors that can be tuned to provide the desired pressure in a syringe. Thus, for a given material, the length and thickness of the band may be sized to achieve a particular force at a given fluid level in the syringe. For example, a typical 20 cc syringe may be filled to the maximum graduation on the syringe (20 ml) which results in a displacement of the plunger flange with respect to the barrel flange. A band may be sized so that when the syringe is empty, the band has no tension and when the syringe is filled to 20 ml, the band stretches in tension to a degree that it applies a force to the plunger cap which results in 90 mmHg of pressure in the fluid in the syringe. In other embodiments, a band may be sized such that it is preloaded with a finite tension when the syringe is empty so that it stays on the plunger flange while still providing the required maximal force when the syringe is filled.

Figure 2B:
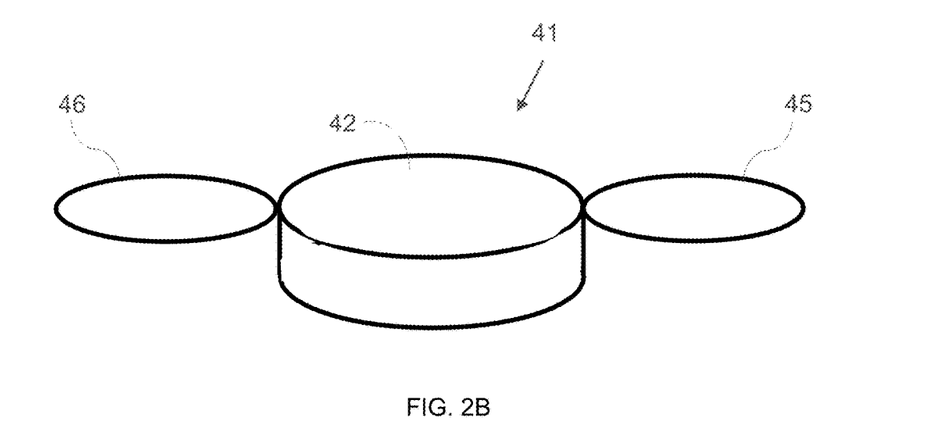
FIG. 2B shows an embodiment of a syringe actuator having two elastic bands.
Figure 2C:
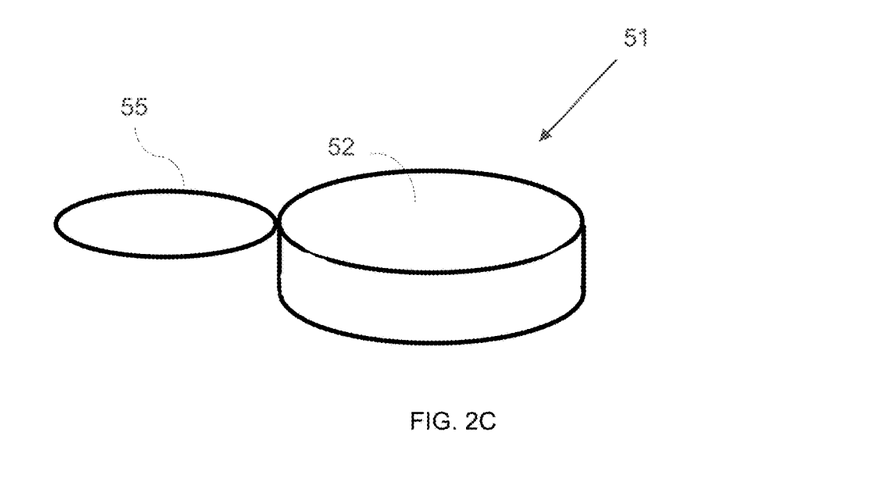
FIG. 2C shows an embodiment of a syringe actuator having one elastic band.

FIG. 2B illustrates another embodiment of a syringe actuator 41 having two elastic bands, a first elastic band 45 and a second elastic band 46 attached to a syringe cap 42, which, as described above, the bands may have the same or differing stiffnesses. This embodiment provides for two levels of hands-free pressure in addition to the capability for an override. In some embodiments, a single band may be attached to the syringe cap 52 as shown in the syringe actuator 51 in FIG. 2C, thus providing one level of pressure when the elastic band 55 is attached to the plunger flange.

Figure 2D:
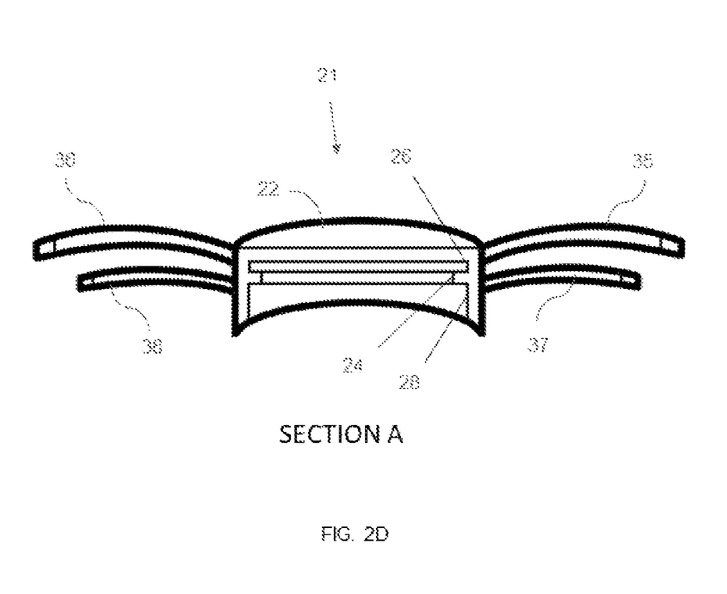
FIG. 2D shows a section view of the embodiment shown in FIG. 2A.

The syringe actuators disclosed herein may be easily attached to the syringe at any time during the procedure, and the bands may be easily attached and released by the operator as needed during the procedure without interfering with the workflow. FIG. 2D shows a cross-sectional view of the syringe actuator 21 embodiment shown in FIG. 2A illustrating the flange section 26 where the plunger flange (not shown) may reside when the syringe actuator 21 is attached to the syringe (not shown). The diameter of the flange section 26 may be the same size as the plunger flange, or it may be slightly larger (loose fit) or slightly smaller (interference fit). In general, a rim 24 (lip) may be provided which captures the plunger flange such that the syringe actuator 21 or the rim 24 deform to allow the plunger flange to seat into the flange section 26 where the plunger flange will be captive. This allows the syringe actuator 21 to stay attached to the syringe without relying on the tension of any of the elastic bands 35, 36, 37, or 38 to keep the syringe actuator 21 in place so that the plunger may be manipulated or extended, for example when filling the syringe, without the added force of the bands. The operator may quickly and easily seat the syringe actuator 21 onto the plunger, for example, by applying thumb pressure to the plunger cap 22. Once attached, the syringe actuator 21 may remain attached, but out of the way of the operator until it is employed to apply pressure. In some embodiments, the rim may not extend throughout the full inner diameter of the plunger cap 22, that is, it may be discrete segments.

In other embodiments, the plunger cap may have a thread to engage with the plunger flange of a syringe. This is possible because in most syringe designs, the plunger flange has a thin wall and is round or has rounded sections that can engage with a female threaded opening. Thus, the operator may secure the plunger cap by twisting, for example with a quarter, half, or full twist to lock the plunger cap into place.

The plunger cap 22 may have a recess 28 to help guide the plunger flange into place so that it may be manipulated past the rim 24 easily. Other embodiments may not have a recess, instead the rim may be exposed at the bottom of the plunger cap 22 so that the plunger flange can be seated directly inside the rim. One skilled in the art would recognize that there are many types of recess, tabs, or engagement features that could exist on the cap to secure the cap onto the plunger flange. These and other modifications and permutations are within the scope of the inventions disclosed herein.

In embodiments disclosed herein, the plunger cap may remain attached to the plunger without any other elements, such as bands, holding it in place. Thus, it is a self-adhering or self-locking cap in that it may be secured without any other assistance. This allows it to stay in place on the syringe so that the various bands can be applied to titrate pressure as needed and the bands may be removed to reduce pressure or to allow the syringe to be filled without resistance; in all such scenarios, the plunger cap stays in place so that it is conveniently ready to engage. Furthermore, as the entire syringe actuator resides solely on the plunger cap when not in use, it cannot block or obscure the barrel so that fluid can be monitored closely. Furthermore, even when the bands are attached, as they do not extend appreciably beyond the barrel flange, the entire barrel is unobstructed.

Figure 3:
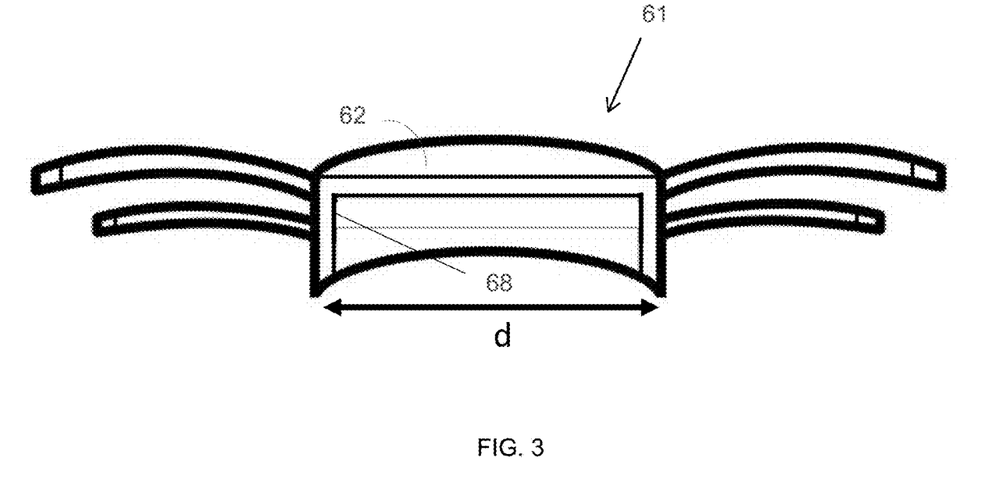
FIG. 3 shows a section view of another embodiment of a syringe actuator.

FIG. 3 shows another embodiment in a similar cross-sectional view as that shown in FIG. 2D. The syringe actuator 61 of FIG. 3 lacks a rim, but the syringe cap 62 has a recess 68 with a diameter designated by "d" that is sized to grip onto the plunger flange of a syringe. The diameter may be undersized to realize an interference fit with the flange. For example, a standard 20 ml Becton Dickenson® syringe has a plunger flange with a diameter of about 19.13 mm, so the recess 68 of the syringe cap 62 may be undersized in diameter by anywhere from fractions of a millimeter or even up to a millimeter or beyond depending on the material composition of the syringe cap 62. One skilled in the art would recognize that more compliant materials may be undersized more than stiffer materials and provide a similar insertion force for applying the syringe cap 62 onto a plunger flange.

The aforementioned embodiments may be fabricated as a unitary component such as, by way of nonlimiting example, by injection molding, compression molding, transfer molding, or silicone molding via HCR (high consistency rubber) molding or LSR (liquid silicone rubber) molding. In such cases, the material may be chosen so that the bands can be sized to achieve the required elasticity to provide the desired force and the syringe cap can be sized so that it is capable of attaching to the plunger flange with reasonable force. In some embodiments, the bands may be a different material from the cap, for example, if the cap is harder or stiffer than the elastic bands. In such cases, the bands may be attached to the cap via slots, grooves, or tabs or they may be overmolded with the cap.

The bands may be made of an elastic material such as a thermoplastic elastomer (TPE), rubber, silicone, or polyurethane by way of nonlimiting example. In embodiments that are manufactured as a unitary component, the syringe cap is made of the same material as the bands. In other embodiments where the syringe cap is made separately or the bands are overmolded, the cap may be made of a more rigid material such as a thermoset or a thermoplastic; candidate materials include but are not limited to polyethylene, polyvinyl chloride, Nylon, or PEEK.

One skilled in the art will recognize that the elastic bands may be made integral to the syringe, such that the cap is not required. That is, in some embodiments, the elastic bands may be molded as part of the plunger, the plunger flange, or the barrel flange or molded connected with other parts of the syringe. Similarly, in other embodiments, the elastic bands may be overmolded along with the plunger, the plunger flange, or other regions of the syringe. Overmolding may be beneficial because the material attributes of the syringe materials could be retained (stiffness, low cost, etc.) while the necessary material properties (e.g., elasticity) of the elastic bands could also be retained. In these embodiments, the operator may use the syringe in a similar manner, having access provided, on the syringe, to one or more attached elastic bands that may be engaged and disengaged throughout a procedure to pressurize the fluid in the syringe. For example, the bands may be permanently attached to the plunger flange (instead of through a cap) in a manner similar to that shown in FIG. 5B so that they attach to the barrel flange when needed; the barrel flange may have hooks or slots to positively retain the elastic bands while allowing them to be removed. Conversely, the elastic bands may be permanently attached to the barrel flange.

Figure 4A:
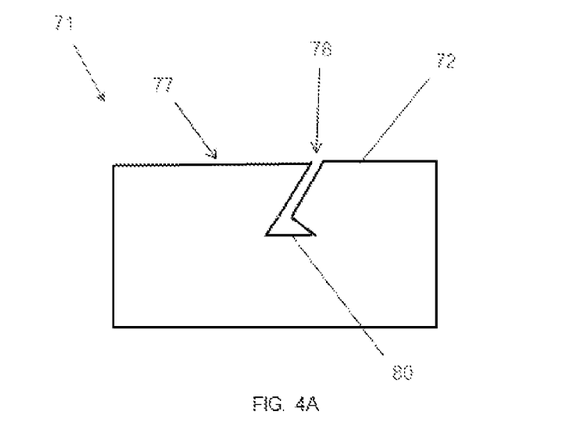
FIG. 4A shows a side view of an embodiment of a syringe actuator.
Figure 4B:
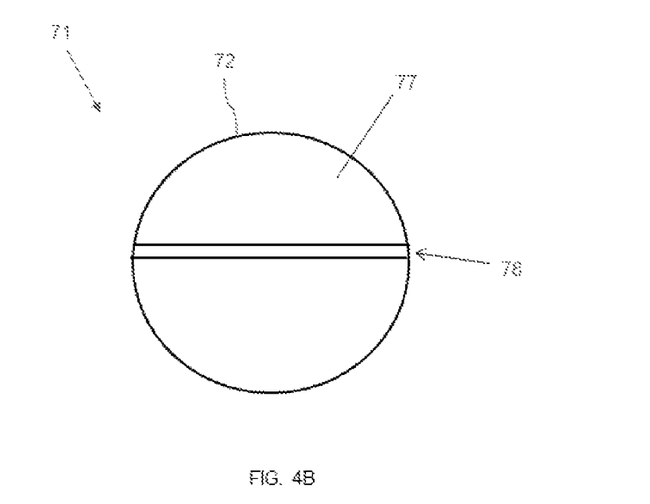
FIG. 4B shows a top view of the embodiment shown in FIG. 4A.
Figure 4C:
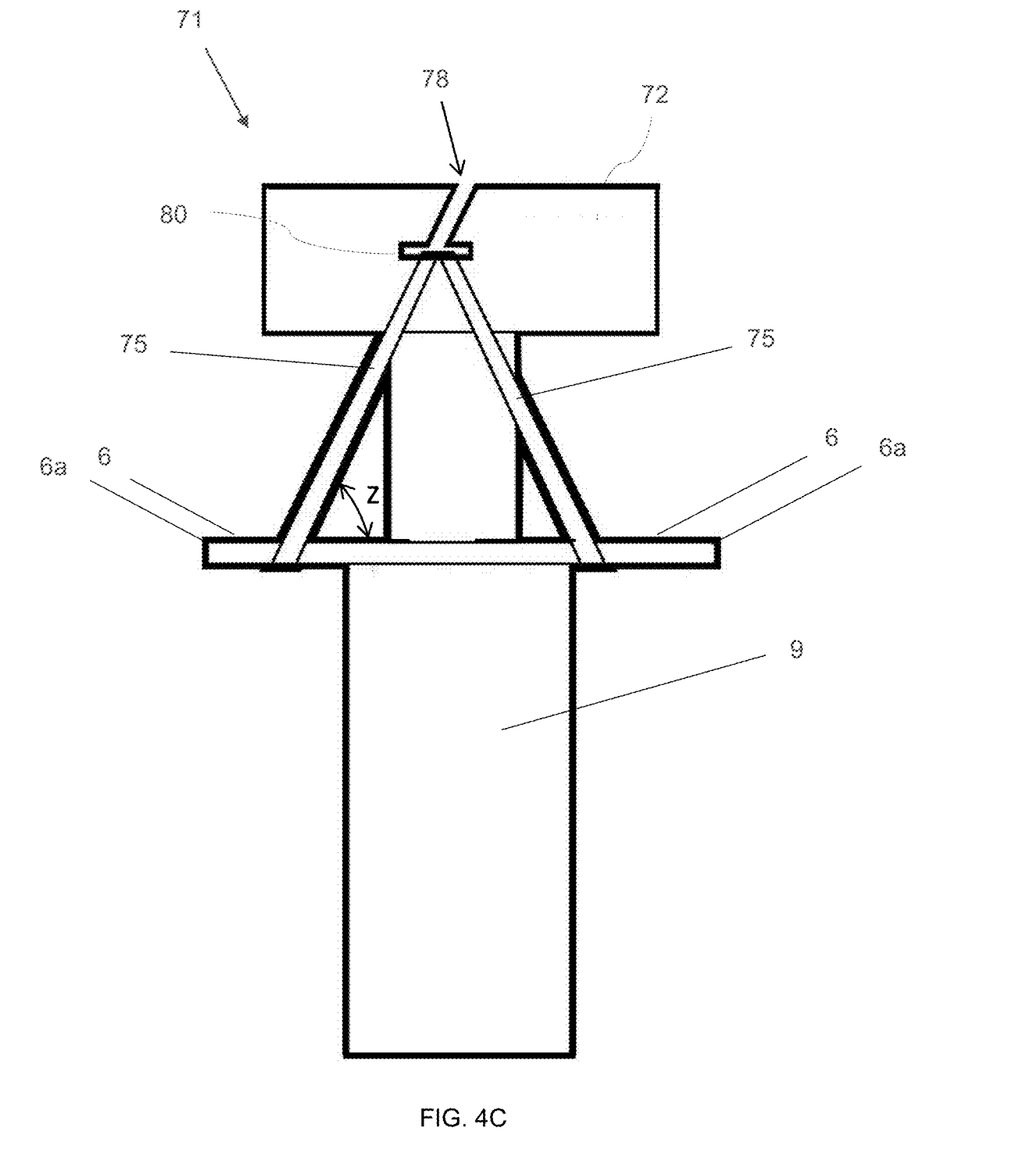
FIG. 4C shows an assembled view of the embodiment shown in FIGS. 4A and 4B.

Another embodiment of a syringe actuator 71 having bands that are separate from the syringe cap 72 is shown in FIGS. 4A-4C. FIG. 4A is a side view of a syringe cap 72 having a slit 78 in a top surface 77 for capturing one or more bands. The slit 78 has a base 80 that may be relatively wider than the slit 78 so that bands (not shown) will tend to be captured once placed through the slit 78. In embodiments where the base 80 is not wider than the slit 78, the bands may still stay in place if the slit 78 is undersized compared to the width of the band, or if the bands are under tension. Significantly, if the bands are captured, they will not fall off while the operator handles the syringe actuator 71 (FIG. 4C) which may disrupt the operator's focus and the procedural flow. As shown in FIG. 4B, the slit 78 may traverse across the top surface 77 entirely from edge-to-edge. One skilled in the art would recognize that there are other locations on a syringe cap for attaching bands; for example, the slits may be located on the sides of the syringe cap or there may be hooks or catches on the sides of the syringe cap for engaging with one or more bands.

In FIG. 4C, the syringe actuator 71 is shown with elastic bands 75 attached to the barrel flange 6 of a syringe barrel 9. The elastic bands 75 are captured in the base 80 of the slit 78 which is centrally located in the syringe cap 72. This central location allows the bands 75 to be oriented at an angle "z" so that they pull away from the outer edge 6a of the barrel flange 6, thus tending to hold the bands 75 in place on the barrel flange 6. The aforementioned embodiments (FIGS. 2A-3) may also have centrally located band attachments similar to the syringe cap 72, that is, the bands may be molded or overmolded such that they are centrally located on the syringe cap to achieve an angle with respect to the barrel flange 6.

Figure 4D:
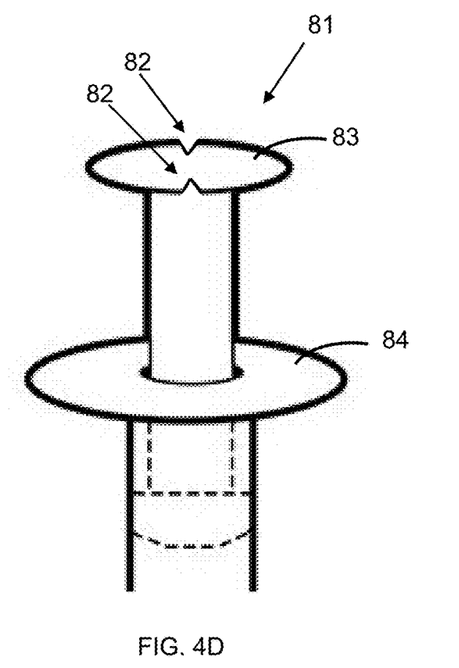
FIG. 4D shows an embodiment of a syringe having elastic band connections on a plunger.
Figure 4E:
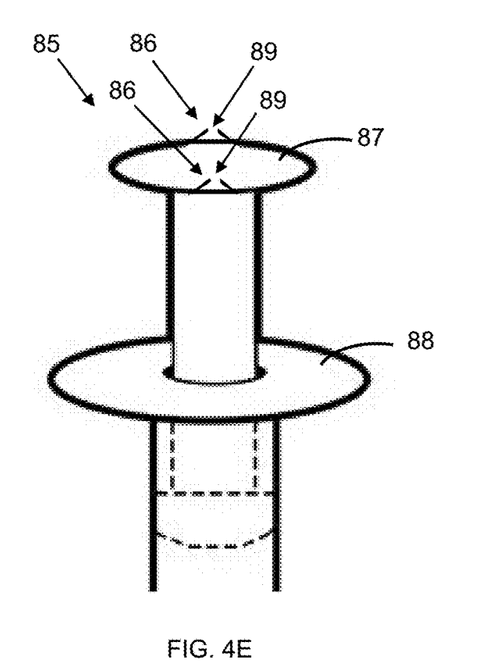
FIG. 4E shows an embodiment of a syringe having elastic band connections on a plunger.
Figure 4F:
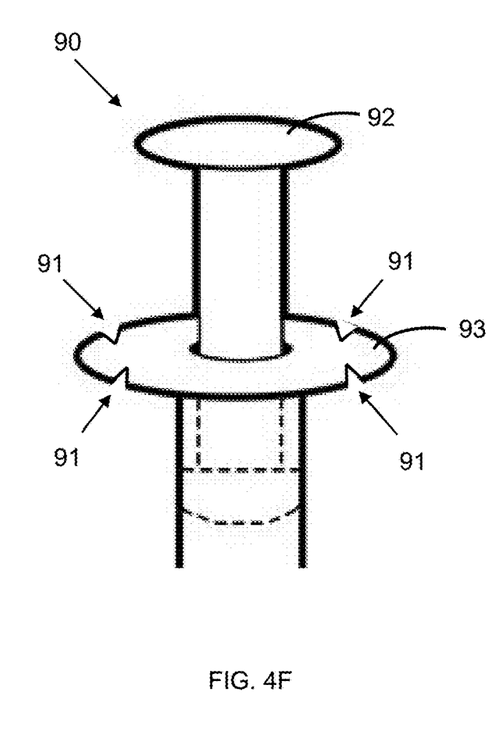
FIG. 4F shows an embodiment of a syringe having elastic band connections on a barrel flange.

As described above for previous embodiments, the bands 75 shown in FIG. 4C, but also disclosed but not shown in FIGS. 4D-4G and other embodiments throughout this disclosure, may be made of an elastic material such as a thermoplastic elastomer (TPE), rubber, silicone, or polyurethane by way of nonlimiting example. The syringe cap 72 may be made of the same material as the bands 75 or it may be made of a more rigid material such as a thermoset polymer or a thermoplastic polymer; some examples include polyethylene, polyvinyl chloride, Nylon, or PEEK In other embodiments, similar band engagement features as those shown in FIGS. 4A-4C may be incorporated directly into a syringe, as shown in FIGS. 4D-4F which show top portions of syringes with different band engagement features. The syringe 81 of FIG. 4D has notches 82 in the plunger flange 83 to engage with bands (not shown) in a similar fashion to the embodiment shown in FIG. 4C. The notches 82 may be simple cutouts or hooked features shaped into the plunger flange 83. Flat features (cutouts) such as the notches 82 preserve the flatness of the plunger flange 83 so that the operator does not feel the notches 82. Each notch 82 may have a narrow entry point to capture the bands more positively so that the bands may remain connected even when removed from the barrel flange 84. The syringe 85 (FIG. 4E) has hooks 86 protruding out of the plunger flange 87 to grasp elastic bands (not shown). The hooks 86 may be low-profile so as not to disrupt the surface when the operator presses on the plunger flange 87 to override the elastic bands, or the hooks 86 may be placed on the underside of the plunger flange 87 so that they cannot be felt. Each hook 86 may have a gap 89 that is narrow so that one or more elastic bands stay captively attached to the plunger flange 87 so that they are available to be attached to the barrel flange 88 when needed.

Figure 4G:
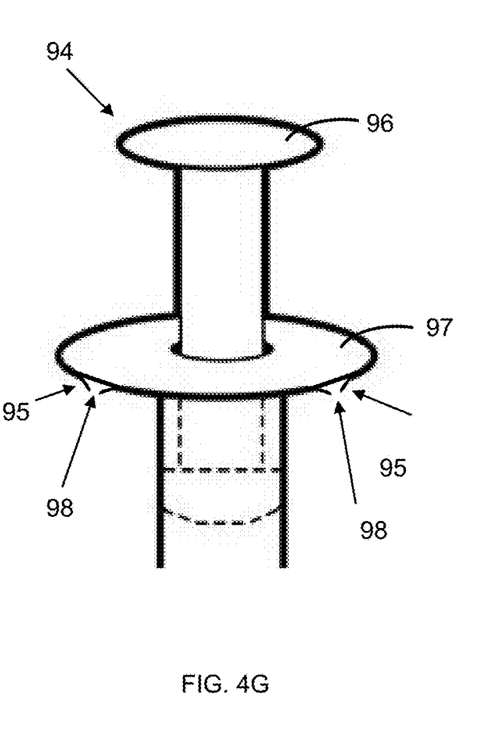
FIG. 4G shows an embodiment of a syringe having elastic band connections on a barrel flange.

Additionally or alternatively, band engagement features may be located on the barrel flange as shown in FIGS. 4F and 4G. The barrel flange 93 of syringe actuator 90 (FIG. 4F) has notches 91 paired on each side of the barrel flange 93 to secure one or more bands on each side of the barrel flange 93. Each notch 91 may have a narrow entry point to capture the bands more positively so that the bands may remain connected even when removed from the plunger flange 92, that is, the bands (not shown) may be held in place on the barrel flange 93 and held free until they are needed, at which time they may be attached to the plunger flange 92 which may have features similar to those shown in FIGS. 4D and 4E for engagement with bands. Finally, FIG. 4G shows an embodiment of a syringe actuator 94 having hooks 95 on the barrel flange 97. The hooks 95 may have gaps 98 that are narrow so that one or more elastic bands stay captively attached to the barrel flange 97 so that they are available to be attached to the plunger flange 96 when needed. It is within the scope of this disclosure that the notches and hooks shown in FIGS. 4D-4F may be on the upper, lower, or edge of the barrel flange or plunger flange. It is also within the scope of this disclosure that both the plunger flange and the barrel flange may have various features for engaging with bands. Furthermore, the syringe may be supplied to the operator in the package with the elastic bands already attached so that they are ready to use when opened in the surgical suite.

One skilled in the art will recognize that the elastic bands may be made integral to the syringe, such that attachment features are not required. That is, in some embodiments, the elastic bands may be molded as part of the plunger, the plunger flange, or the barrel flange or molded connected with other parts of the syringe. Similarly, in other embodiments, the elastic bands may be overmolded along with the plunger, the plunger flange, or other regions of the syringe. In these embodiments, the operator would use the syringe in a similar manner, having access provided, on the syringe, to one or more attached elastic bands that may be engaged and disengaged throughout a procedure to pressurize the fluid in the syringe.

Various embodiments of a method or technique to employ a syringe actuator in the context of the preparation of a coronary bypass conduit harvested from a patient will now be described. The systems, devices, and methods described can be used to assist in flushing harvested vessels and in diagnosing and repairing vessel leaks in the vessels. However, the methods and devices described herein may be applicable to other applications where conduits are treated in similar ways. The order of steps and components described herein is for illustrative purposes only and is not intended to limit the scope of the invention(s), as various alternative combinations or permutations of the sequence of steps are contemplated.

Figure 5A:
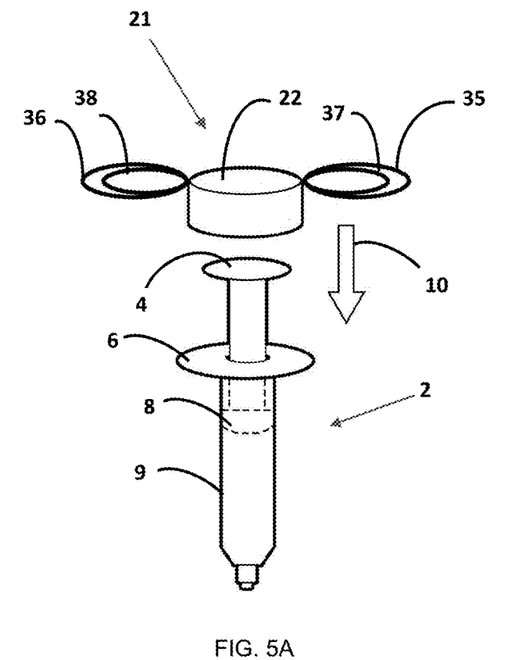
FIG. 5A shows a syringe actuator being attached to a syringe.
Figure 5B:
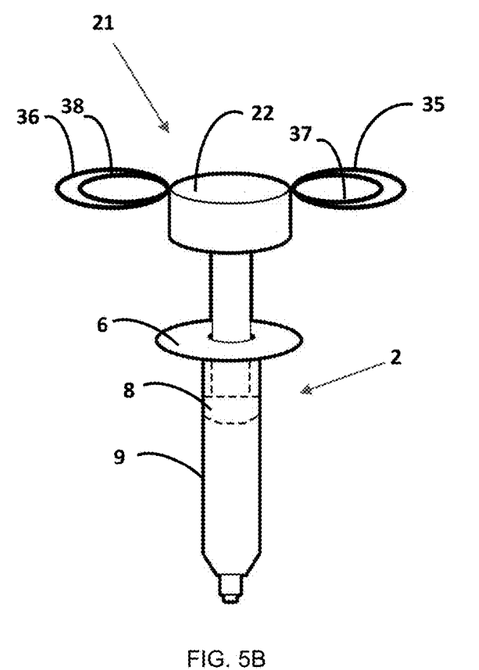
FIG. 5B shows the syringe actuator of FIG. 5A attached to a syringe.
Figure 5C:
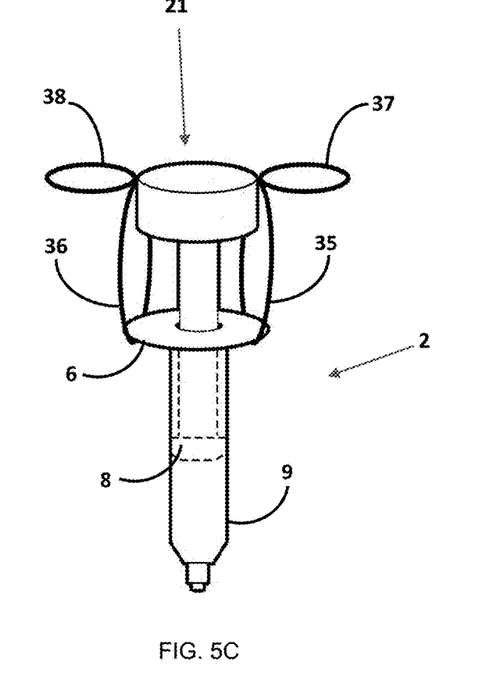
FIG. 5C shows a syringe actuator of FIG. 5A with two elastic bands engaged.

FIGS. 5A-5C illustrate the application of the syringe actuator 21 to a syringe 2. In FIG. 5A, the syringe actuator 21 is placed down, indicated by arrow 10, where it engages with the plunger flange 4 as described above. In FIG. 5B, the syringe actuator 21 is attached to the syringe 2 while the elastic bands 35, 36, 37, and 38 are unengaged but not loose such that they can fall off or otherwise disrupt the procedure, that is, they are constrained to the plunger cap 22 and remain ready to be applied when the operator is ready to engage them. Having additional components lying around in the limited space of a sterile surgical field, such as loose bands, may distract the operator from focusing on the critical task at hand—preparing the conduit. When the operator engages the syringe actuator 21, with two of the bands 35 and 36 as shown in FIG. 5C, a force is applied to the plunger flange, and the fluid is pressurized by an amount set by the elasticity of the bands 35 and 36. The piston 8 will translate along the barrel 9 if there is no fluid blocking element, such as a stopcock, in place, but if the fluid flow is blocked by a stopcock or a clamped conduit, the pressure in the fluid will rise. In between these states are the leaking conduit scenarios where the pressure rises resulting in some displacement of the piston 8 and the fluid. Precise manual control of the procedure may be required wherein the operator adjusts a stopcock, the bands, and the override pressure iteratively while monitoring the piston, fluid flow, and leaks, as described in more detail below.

During the examination of a conduit, it is important for the operator to see small movements of fluid in the barrel 9 to discern leaks; a clear, unobstructed, barrel 9 allows the operator to see the fluid move with respect to the graduations on the barrel 9. It is notable that, when a syringe is at least partially filled with fluid, the bands 35, 36, 37, and 38 do not extend appreciably beyond the barrel flange 6; this leaves the barrel 9 unobstructed so that the operator can see the fluid and the volume markings on the barrel 9. Furthermore, in embodiments, the syringe actuator, including the elastic bands, does not touch the tip of the syringe in any way so that it does not interfere with attachments, such as a stopcock, that may be attached and removed frequently during the procedure during syringe refill, for example. The syringe actuator 21 does not need to be removed when the syringe 2 is filled, or when syringe attachments are changed, because the bands 35 and 36 may be left engaged entirely, or they may be removed from the barrel flange 6 and they will stay in place because they are attached to the plunger cap 22.

Figure 6A:
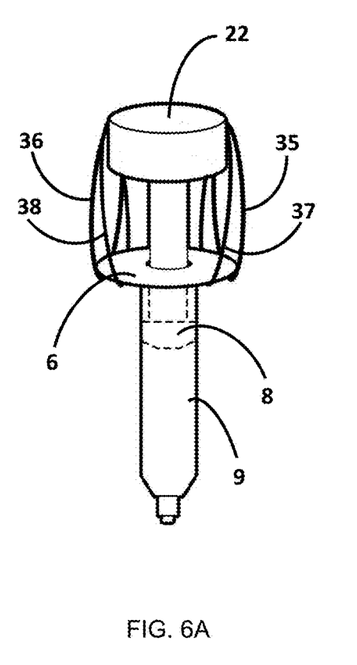
FIG. 6A shows a syringe actuator attached to a syringe with four bands engaged.
Figure 6B:
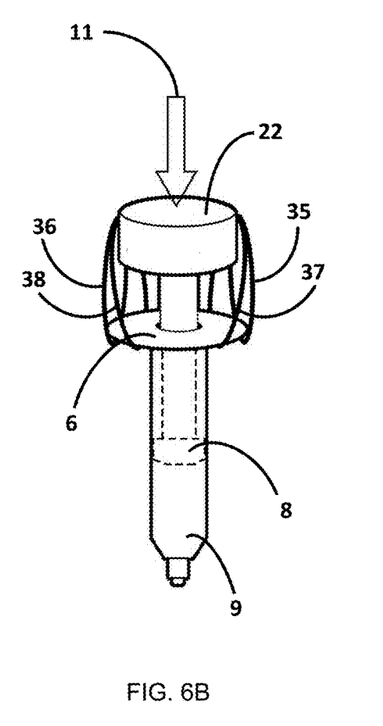
FIG. 6B shows a syringe actuator attached to a syringe with a force override applied to the plunger cap.
Figure 6C:
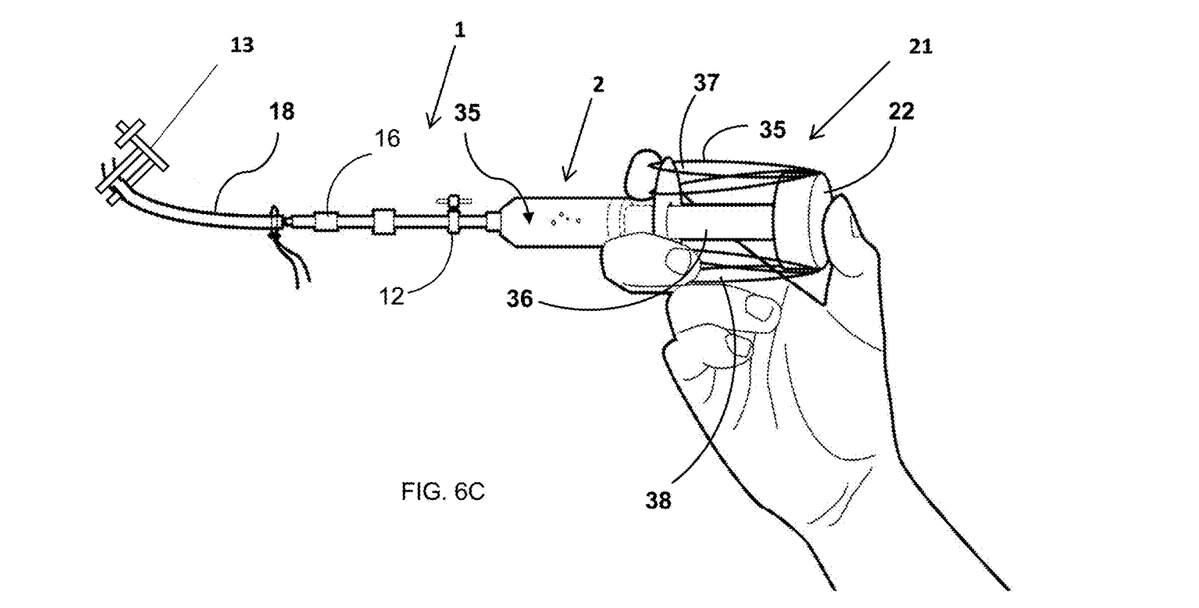
FIG. 6C shows a conduit distention system with a force override applied to the syringe actuator.

FIGS. 6A-6C show the syringe actuator 21 with all four bands 35, 36, 37, and 38 configured to apply maximum pressure. In some cases, the operator may desire to add incrementally more pressure while working on a conduit; in this case the operator may override the pressure by applying a force to the plunger cap 22 as illustrated by the force arrow 11 in FIG. 6B which shows the piston 8 extending further down the barrel 9. FIG. 6C shows the syringe actuator 21 in the context of a conduit distention system 1 having a syringe 2, stopcock 12, cannula 16, and a vein 18 with a soft clamp 13 at the distal end. Thus, the operator may override the syringe actuator to incrementally assess the vein 18 for leaks while perceiving feedback from the syringe. The various syringe actuator embodiments preserve the ability for the operator to use manual override and feel concomitant tactile feedback pressure when needed.

Figure 7:
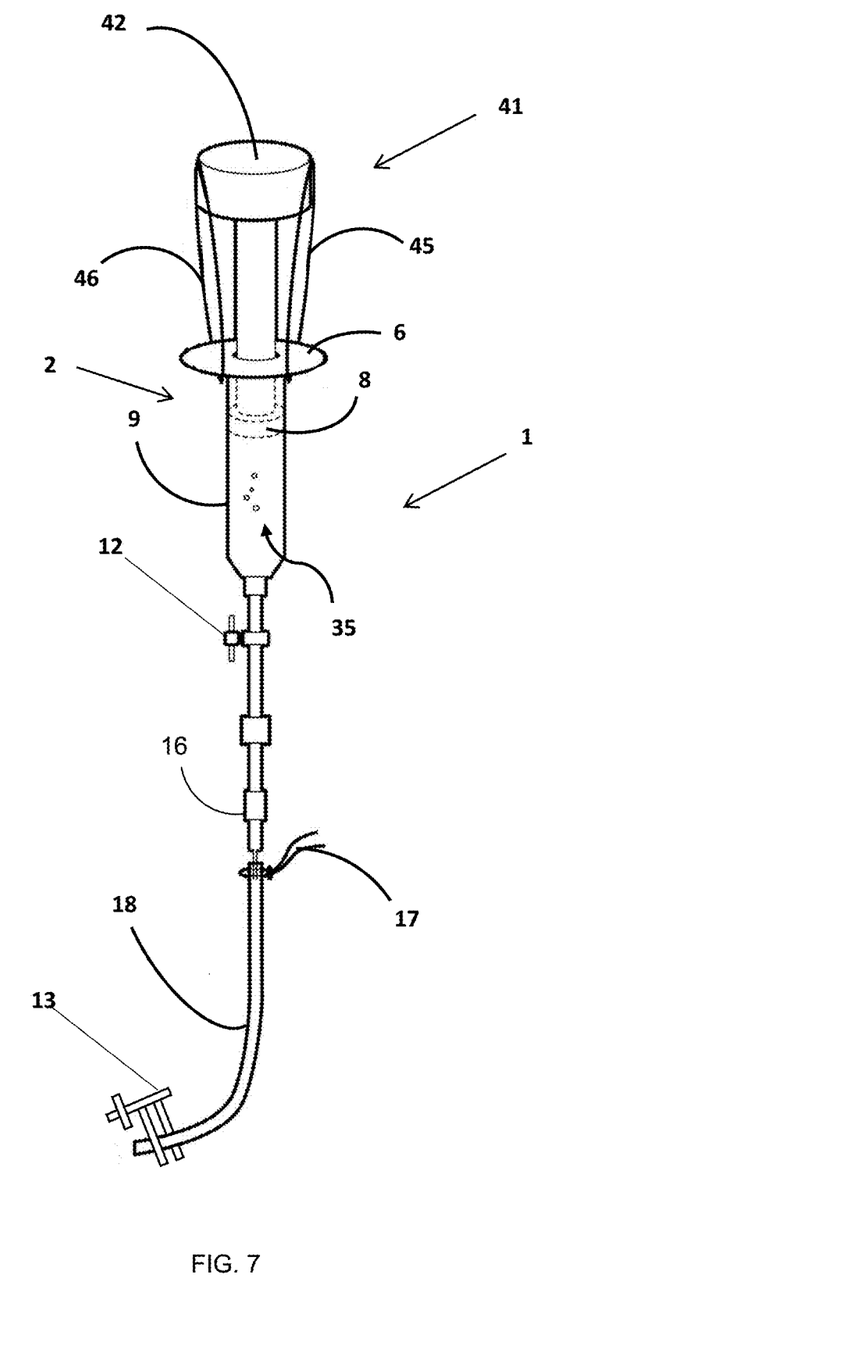
FIG. 7 shows an embodiment of a conduit distention system.

As part of a cardiovascular bypass procedure, a segment of the saphenous vein, of the required length, is removed from the body and prepared on the sterile field for implantation as a graft into the heart. Once removed, the vein is attached to a cannula and syringe system for flushing with fluid (typically saline) and leak diagnosis in what is a generally iterative process to find and repair leaks. FIG. 7 shows a conduit distention system 1 with an attached syringe actuator 41 and an attached vein 18 (conduit) for reference. Although the elastic bands 45 and 46 are shown attached to the barrel flange 6 in FIG. 7, this figure is only for reference in describing the procedure, and the bands may be in various states of attachment throughout the procedure. Referring to the flowchart in FIG. 8, in step 100, the syringe actuator 41 is attached to the plunger flange (not shown), leaving the elastic bands 45 and 46 loose; thus, the elastic bands 45 and 46 are attached to the syringe 2 and ready for use. Next, the syringe is filled with fluid to 20 cc (step 101), and the syringe 2 is connected to the vein cannula (step 102) (for example, using a suture 17). In some embodiments, depending on operator preference and technique, the conduit distention system 1 has a stopcock 12 attached distally to the syringe 2 to enable more fine control.

Figure 8:
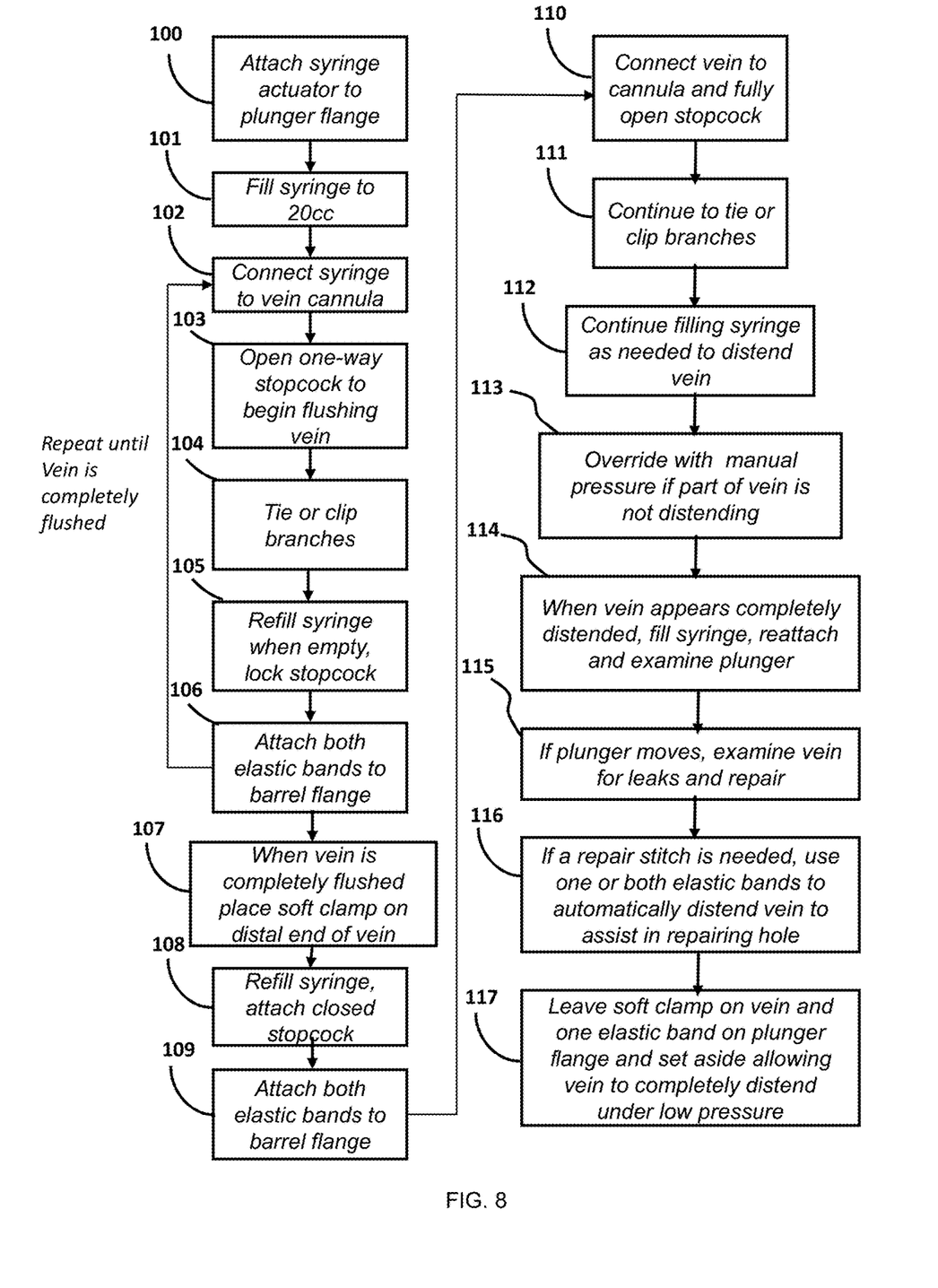
FIG. 8 is a flowchart of an embodiment of a method for preparing a harvested vein.

Next, the stopcock 12 is opened to begin automatically flushing the conduit (step 103). The stopcock 12 may be adjusted to control the amount of flow that is used to flush the vein 18 and to help to identify branches to clip or tie. This initial flush may be conducted by pressing the syringe by hand or by attaching the elastic bands 45 and 46. Next, the branches are tied or clipped (step 104), and if there is too much fluid escaping from the branches or end of vein 18, the rate of fluid flow may be reduced by adjusting the stopcock 12.

When the syringe 2 becomes empty, it is refilled to 20 cc and the stopcock 12 is locked (step 105). Next, the first elastic band 45 and second elastic band 46 may be placed onto the barrel flange 6 (step 106). Repeating back to step 103, the syringe 2 may be connected, with the stopcock 12, to the vein cannula 16, and the stopcock 12 may be opened to continue automatically flushing the vein 18 (step 103) while tying or clipping branches (step 104). Again, the stopcock 12 may be adjusted to control the amount of flow used to flush the vein 18 and to identify branches to clip or tie.

When the vein 18 is completely flushed, a soft clamp 13 may be placed on the distal end of vein 18 (step 107) to block flushing out of the distal end of the vein (18). Next, the syringe may be refilled to 20 cc (step 108) and the closed stopcock attached to prevent flow, both elastic bands 45 and 46 may be attached over the barrel flange 6 (step 109), and the vein 18 may be connected to the cannula 16 at which point the stopcock 12 may be fully opened (step 110). This will cause the vein 18 to begin to gently distend at which point the operator may continue tying or clipping all branches (step 111) and continuing to fill the syringe 2 with fluid as needed to completely distend the vein 18 (step 112).

If there is a section of vein 18 that is not distending, the vein 18 may be set off to the side to allow it to gently fully distend at a maximum pressure of 180 mmHg, for example, or the operator may gently override the pressure with his or her thumb to distend the section (step 113). This typically does not take much additional pressure and the operator may rely on tactile and visual feedback while performing this step.

When vein 18 appears completely distended, the syringe 2 is filled to 20 cc, reattached, and the plunger 5 examined for movement (step 114). If the plunger 5 moves and fluid is still emptying into the vein 18, the vein 18 may be placed on a towel and examined for areas that are getting moist on the towel to find a branch or hole in the vein 18 to repair (step 115).

If there is a repair stitch needed, one or both elastic bands 45 and 46 may be applied to flush fluid the hole to assist in identifying and repairing the hole (step 116); the attached bands 45 and 46 eliminate the need to have an additional person distend the vein while it is being repaired and the operator is free to adjust the stopcock to control the flow through the hole to assist in making the repair.

Finally, a soft clamp 13 may be left on the vein 18, and one elastic band 45 may be attached to the barrel flange 6 and the conduit distention system 1 may be set aside allowing the vein 18 to completely distend under low pressure as summarized in step 117.

While the method illustrated above was described with reference to the embodiments having the elastic bands attached to the plunger cap, the method can also be performed using other embodiments, such as that shown in FIGS. 4D-4F which are embodiments having the elastic band connections located directly on the flanges of the syringe.

While this invention has been particularly shown and described with references to example embodiments thereof, it will be understood by those skilled in the art that various changes in form and details may be made therein without departing from the scope of the invention(s) encompassed by the appended claims. While the above is a complete description of the certain embodiments of the invention, various alternatives, modifications, and equivalents may be used. The various devices and method steps of the embodiments disclosed herein may be combined or substituted with one another, and such alternative embodiments fall within the scope of the claimed invention(s). Therefore, the above description should not be taken as limiting in scope of the invention (a) which is defined by the appended claims.

What is claimed is:

1. A device for actuating a syringe, the device comprising: a cap having a proximal end and a distal end; a rim in a distal end of the cap, wherein the cap is configured to deform to allow a plunger flange of the syringe to seat under the rim enabling the device to be retained on the syringe solely by the connection between the plunger flange and the rim; and at least one elastic band connected to the cap, the elastic band capable of connecting to a barrel flange of the syringe to apply a force between the cap and the barrel flange.

2. The device of claim 1, wherein the at least one elastic band comprises a first elastic band connected to a first side of the cap and a second elastic band connected to an opposite side of the cap, and wherein each elastic band may be individually attached to the barrel flange to apply different forces to the plunger flange.

3. The device of claim 1, wherein the cap and the at least one elastic band are made as one unitary part.

4. The device of claim 3, wherein the unitary part is made by injection molding.

5. The device of claim 4 wherein the unitary part is made of a thermoplastic elastomer.

6. A method for preparing a conduit, the method comprising:
providing the device of claim 1;
attaching the cap to a plunger flange of a syringe;
filling the syringe with fluid;
connecting the syringe to a stopcock and a vein cannula;
attaching at least one elastic band to the barrel flange of the syringe to apply pressure to the fluid in the syringe;
opening the stopcock to flush the conduit;
tying or clipping branches of the conduit that are leaking;
placing a soft clamp on a distal end of the conduit;
removing the at least one elastic band from the barrel flange while keeping the cap attached to the plunger flange;
refilling the syringe and closing the stopcock;
attaching at least one elastic band to the barrel flange; and
tying or clipping branches that are leaking.

7. The method of claim 6 further comprising the steps of:
overriding the pressure applied by the elastic band by pressing on the cap;
removing the at least one elastic band from the barrel flange;
refilling the syringe;
attaching one elastic band to the barrel flange; and
allowing the conduit to completely distend under low pressure.

8. The method of claim 6, wherein the cap is capable of fitting onto the plunger flange by an interference fit.

9. The method of claim 6, wherein the at least one elastic band comprises a first elastic band connected to a first side of the cap and a second elastic band connected to an opposite side of the cap, and wherein each elastic band may be individually attached to the barrel flange to apply different forces to the plunger flange.

10. The method of claim 6, wherein the cap and the at least one elastic band are made as one unitary part.

11. The method of claim 10, wherein the unitary part is made by injection molding.

12. The method of claim 11 wherein the unitary part is made of a thermoplastic elastomer.

13. A method for preparing a conduit, the method comprising:
providing a syringe having a plunger flange and a barrel flange, wherein the plunger flange has at least one elastic band permanently attached;
filling the syringe with fluid;
connecting the syringe to a stopcock and a vein cannula;
attaching the at least one elastic band to the barrel flange of the syringe to apply pressure to the fluid in the syringe;
opening the stopcock to flush the conduit;
tying or clipping branches of the conduit that are leaking;
placing a soft clamp on a distal end of the conduit;
removing the at least one elastic band from the barrel flange;
refilling the syringe and closing the stopcock;
attaching at least one elastic band to the barrel flange; and
tying or clipping branches that are leaking.

14. The method of claim 13 further comprising the steps of:
overriding the pressure applied by the elastic band by pressing on the plunger flange;
removing the at least one elastic band from the barrel flange;
refilling the syringe;
attaching one elastic band to the barrel flange; and
allowing the conduit to completely distend under low pressure.

15. The method of claim 13, wherein the at least one elastic band comprises a first elastic band connected to a first side of the plunger flange and a second elastic band connected to an opposite side of the plunger flange, and wherein each elastic band may be individually attached to the barrel flange to apply different forces to the plunger flange.

16. The method of claim 13, wherein the plunger flange and the at least one elastic band are made as one unitary part.

17. The method of claim 16, wherein the unitary part is made by injection molding.

18. The method of claim 13 wherein the at least one elastic band is overmolded with the plunger flange.

* * * * *